United States Patent
Wolber et al.

(10) Patent No.: US 8,478,545 B2
(45) Date of Patent: Jul. 2, 2013

(54) IDENTIFICATION OF ABERRANT MICROARRAY FEATURES

(75) Inventors: Paul Kenneth Wolber, Los Altos Hills, CA (US); Robert Page, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 70 days.

(21) Appl. No.: 13/152,602

(22) Filed: Jun. 3, 2011

(65) Prior Publication Data

US 2012/0310537 A1 Dec. 6, 2012

(51) Int. Cl.
*G06F 19/00* (2011.01)
*G11C 17/00* (2006.01)
*C12Q 1/68* (2006.01)

(52) U.S. Cl.
USPC .................................. 702/20; 365/94; 435/6.1

(58) Field of Classification Search
None
See application file for complete search history.

(56) References Cited

PUBLICATIONS

Delenstarr, et al., "Estimation of the confidence limits of oligonucleotide microarray-based measurements of differential expression", 2001, 4266:120-31.

*Primary Examiner* — John S Brusca

(57) ABSTRACT

Described herein is a method for identifying an aberrant feature on a nucleic acid array. In general terms, the method comprises: a) obtaining a log transformed normalized value indicating the amount of hybridization of a test sample to a first feature on the nucleic acid array; b) calculating a z-score for the first feature using: the log transformed normalized value; and the distribution of reference log transformed normalized values that indicate the amount of hybridization of control samples to the same feature on a plurality of reference arrays; and c) identifying the test feature as aberrant if it has a z-score that is above or below a defined threshold.

17 Claims, 7 Drawing Sheets

IDENTIFICATION OF ABERRANT MICROARRAY FEATURES

INTRODUCTION

In the analysis of arrays, it is important to identify and flag aberrant features, i.e., features that exhibit unusual statistical or morphological properties, in order to avoid contamination of a microarray dataset with poor quality data. This disclosure relates to a method of identifying aberrant microarray features.

SUMMARY

Described herein is a method for identifying an aberrant feature on a nucleic acid array. In general terms, the method comprises: a) obtaining a log transformed normalized value indicating the amount of hybridization of a test sample to a first feature on the nucleic acid array; b) calculating a z-score for the first feature using: the log transformed normalized value; and the distribution of reference log transformed normalized values that indicate the amount of hybridization of control samples to the same feature on a plurality of reference arrays; and c) identifying said test feature as aberrant if it has a z-score that is above or below a defined threshold.

DEFINITIONS

Figure 1:
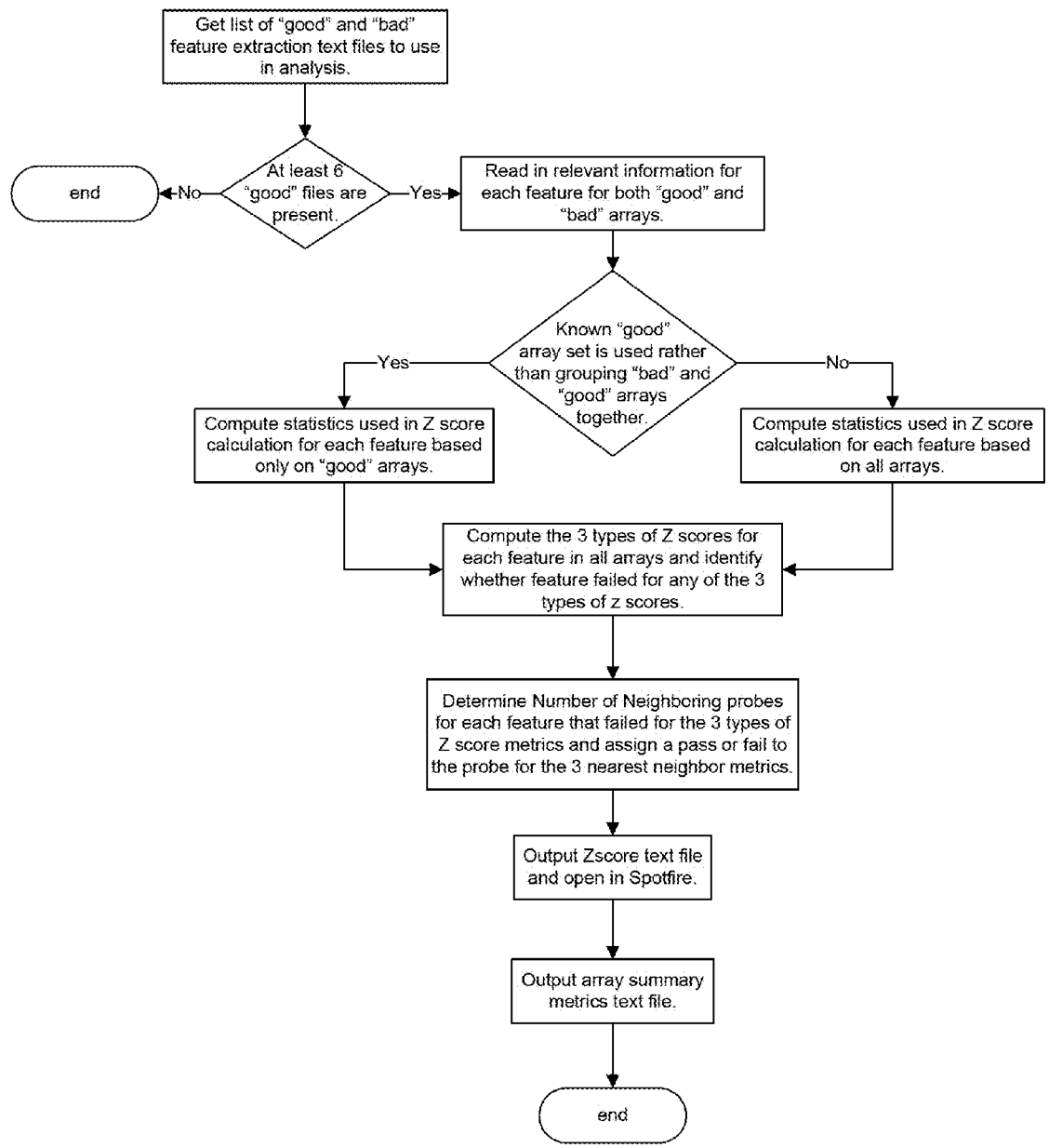
FIG. 1 is a flow chart illustrating some aspects of one embodiment of the subject method.

The term "sample", as used herein, refers to a material or mixture of materials, typically, although not necessarily, in liquid form, containing one or more nucleic acid (DNA or RNA) analytes of interest.

The term "biologically derived sample", as used herein, refers to a nucleic acid sample that is made from or derived from living cells. Sample made from a tissue from an organism (e.g., a biopsy or the like) or a cell line (including frozen or stored versions of the same) are examples of biologically derived samples.

The term "non-biologically derived sample", as used herein, refers to a nucleic acid sample that is made up of pre-defined synthetically made oligonucleotides. An example of a non-biologically derived sample is described in US patent application publication no. US20060121491.

The term "test sample" as used herein, refers to a sample that is under study.

The term "control sample", as used herein, refers to a sample that is comparable to the test sample. As will be described in greater detail below, relative to a test sample, a control sample may be, e.g., a different aliquot of the same sample; from the same tissue, or from the same cell line.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer that can be of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, uracil and thymine (G, C, A, U and T, respectively).

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

The term "probe," as used herein, refers to a nucleic acid that is complementary to a nucleotide analyte of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional and three-dimensional arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323, 043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a feature (i.e., an "element" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

As used herein, the term "aberrant feature" is a feature that has an unusual statistical or morphological property. Aberrant features may be caused by, e.g., problems that occur during array synthesis (e.g., incomplete coupling chemistry), array storage, array handling, hybridization or scanning, for example.

As will be described in greater detail below, in certain cases features on different arrays will be described as being "corresponding" as one another. For example, data may be obtained from a first feature on one array as well as corresponding features on other arrays. In these cases, features that correspond to one another have the same probe sequence. As such if a first feature on one array has corresponding features on other arrays, the first feature and the corresponding features have the same probe.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "data" refers to a collection of organized information, generally derived from results of experiments in lab or in silico, other data available to one of skilled in the art. Data may be in the form of numbers, words, annotations, or images, as measurements or observations of a set of variables. Data can be stored in various forms of electronic media as well as obtained from auxiliary databases.

As used herein, the term "obtaining", as used in the context of obtaining data, is to be interpreted broadly to mean any means for coming into possession of data, including accessing a file that stores data, receiving data, and producing data (e.g., performing an experiment).

As used herein, the term "plurality" refers to at least 2, e.g., at least 5, at least 10, at least 20, at least 50, at least 100, at least 500, at least 1,000, at least 5,000 or at least 10,000 or more, up to 50,000, or 100,000 or more.

As will be described in greater detail below, a feature may be called as aberrant if it has a z-score that is "above or below a defined threshold". Determining whether a feature is aberrant method generally involve comparing the z-score for that feature to another number (the defined threshold) to determine the z-score is above or below the defined threshold. A feature may be aberrant if: a) it has a z-score that is below a defined threshold (i.e., when the defined threshold is a negative number (e.g., −6) and features having a z-score below that negative number are aberrant); b) it has a z-score that is above a defined threshold (e.g., when the defined threshold is a positive number (e.g., 6) and features having a z-score above that number are aberrant). Determining whether a z-score is "above or below a defined threshold" includes determining if a z-score is in a defined range or outside of a defined range, as well as determining whether than a z-score is greater/less than or equal to a defined threshold. A defined threshold can be defined empirically, theoretically or arbitrarily, for example.

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The method described in greater detail below may be generally employed in the analysis of array data (e.g., gene expression or CGH data) in which the amount of a particular nucleic acid analyte (RNA or DNA) in a nucleic acid sample is assayed. In general, these assays employ the following steps: a) labeling the nucleic acid sample, b) contacting the labeled sample with a probe for an analyte to the sample under conditions sufficient for specific binding to occur between the probe and the analyte; and c) identifying the amount of label in the resultant analyte/probe complex, thereby determining the amount of the analyte in the sample. Such methods are generally known.

Specifically, a labeled sample is applied to a substrate that includes at least one probe, and incubated under conditions suitable for an analyte/probe complex, e.g. a nucleic acid duplex (i.e. a RNA/RNA, DNA/RNA, or DNA/DNA duplex) to be formed between a probe and a labeled analyte in the sample, if such a labeled analyte is present. In certain embodiments, the substrate that includes the probe is an array of probes, where each probe is contained in a feature of the array, and where an array includes at least about 20, at least about 50, at least about 100, at least about 200, at least about 500, at least about 1,000, at least about 2,000, at least about 5,000, at least about 10,000, at least about 20,000, at least about 50,000, usually up to about 100,000 or more features.

After incubation, labeled sample that is not bound with a probe is typically washed away from the substrate, and the substrate, now including the labeled analyte/probe duplexes, is scanned by an instrument capable of quantitatively measuring the bound label, e.g. a scanning fluorometer. The amount of each label associated with features of the array (each feature containing, e.g., a target analyte/probe complex or a probe if no target analyte is present) is then determined. In some embodiments, the substrate is scanned in two channels corresponding to the distinguishing features of the probes, such that the amounts of two distinguishable labels associated with each feature are determined independently (i.e. without interference) from other labels. In certain embodiments, scanning results in two scans, one for each channel, and usually represents a pixilated image of the substrate that reflects the amount of label associated with the features of the substrate. For example, each pixel of the image is accorded a signal level that represents the level of brightness of the label signal. Data from only one channel need be used in the method below. As mentioned above, scanning methods are well known in the art (e.g., DeRisi et al. Science 278:680-686, 1997), and several suitable scanners are commercially available from Perkin-Elmer, Agilent, or Axon Instruments, etc., and are described in U.S. Pat. Nos. 5,091, 652; 5,760,951, 6,320,196 and 6,355,934), the disclosures of which are herein incorporated by reference.

Feature extraction is the method by which numerical data is obtained from an array. In general feature extraction methods involve identifying a feature (usually corresponding to a probe) on a scan of a hybridized array, and measuring the amount of label (e.g., fluorescence) that is associated with the feature. In most embodiments, feature extraction methods provide a numerical figure for each features of an array. Several commercially available programs perform feature extraction on microarrays, such as IMAGINE® by BioDiscovery (Marina Del Rey, Calif.) Stanford University's "ScanAlyze" Software package, Microarray Suite of Scanalytics (Fairfax, Va.), "DeArray" (NIH); PATHWAYS® by Research Genetics (Huntsville, Ala.); GEM Tools® by Incyte Pharmaceuticals, Inc., (Palo Alto, Calif.); Imaging Research (Amersham Pharmacia Biotech, Inc., Piscataway, N.J.); the RESOLVER® system of Rosetta (Kirkland, Wash.) and the Feature Extraction Software of Agilent Technologies (Palo Alto, Calif.). Values corresponding to the amount of label associated with features of an array are produced using feature extraction software, as described above. A value may be measured as a quantitative (i.e. absolute) value of signal, or a qualitative (e.g. relative) value of signal, as is known in the art.

The present method makes use of three statistical techniques to rescale the signal from a given feature on a given array in such a way that all signals from all features of all arrays in a group of arrays are measured on the same scale.

The optional first step of the method involves identification of a subset of "control" arrays. Such identification may be performed on the basis of some objective indicator of array data quality (e.g. % CV), or some other array property (e.g. array manufacturing time period). This first step is not essential; if defects affect different regions of different arrays, then the data for a given feature will be "normal" on most arrays. However, the identification and use of an appropriate control set of "normal" arrays may improve the sensitivity of the method, particularly for arrays with many aberrant features.

In the second step of the method, values (i.e., the amount of signal obtained from the feature) are normalized. The standard method of signal normalization is division of all signals from non-control probes in a given color channel on a given array by, e.g., the $75^{th}$ percentile signal for non-control probes in that color channel on that array, although other methods may be used. This transformation eliminates proportional signal differences between arrays caused by different sample labeling efficiencies, different hybridization efficiencies, differences in microarray scanner gain, etc.

For example, normalization may involve multiplying each numerical value for one data group by a value that allows the direct comparison of those amounts to amounts in a second data group. Several normalization strategies have been described (Quackenbush et al, Nat. Genet. 32 Suppl:496-501, 2002, Bilban et al Curr Issues Mol Biol. 4:57-64, 2002, Finkelstein et al, Plant Mol Biol. 48(1-2):119-31, 2002, and Hegde et al, Biotechniques. 29:548-554, 2000). Specific examples of normalization suitable for use in the subject methods include linear normalization methods, non-linear normalization methods, e.g., using lowess local regression to paired data as a function of signal intensity, signal-dependent non-linear normalization, qspline normalization and spatial normalization, as described in Workman et al., (Genome Biol. 2002 3, 1-16).

In the third step, the normalized values are log transformed (e.g., using $\log_2$, but log to any base may be used). Values from repeated, identical features do not usually yield a Normal (i.e. Gaussian) distribution of values. However, the logarithms of the signals are approximately normally distributed. Transformation of signals into a form that is approximately normally distributed allows the valid use of standard statistical measures of distribution properties, such as average (mean) and standard deviation, in subsequent steps. Alternatively or in addition, measures that do not assume a normal distribution, such as median and inter-quartile range, could be used in subsequent steps.

In the fourth step, the mean and standard deviation for the normalized, log-transformed signal of each feature in the control set of arrays are calculated. This calculation quantifies the center and width of the distribution of log-transformed, normalized signals from each feature of a population of properly functioning arrays. Note that, if the distribution of log-transformed, normalized signals is Gaussian, the mean and standard deviation parameters completely determine the distribution. Alternatively, robust rank-order statistical measures such as median (in place of mean) and inter-quartile range, IQR (in place of standard deviation) may be calculated. In this case, IQR should be scaled, i.e. 0.74*IQR should be used, since, for a Gaussian distribution, standard deviation=0.74*IQR.

In the next step, a z-score statistic is calculated for each feature of a test array. The z-score is a statistical metric that expresses the difference between a quantity and the mean (or median) of that quantity in units of the standard deviation (or IQR):

$$Z_{i,j} = \frac{S_{i,j} - \mu_S}{\sigma_S}.$$

where S is the log-transformed, normalized signal, $\mu_S$ is the mean (or median) of S, $\sigma_S$ is the standard deviation (or 0.74*IQR) of S, and the indices i and j track array and feature number, respectively. Similar scores can be calculated for other metrics of a distribution. In general, all signals are transformed to the same scale, which measures where a particular value of the signal from a particular feature lays in the distribution of signals observed from that feature in properly functioning arrays.

Transforming to the z-score statistic enables clear identification of aberrant features or groups of such features via visual or computer-assisted identification of features with unusually positive or negative z-scores. The z-score is a pure, unitless number with a standard interpretation: it measures the number of standard deviations away from the mean of a distribution that some member of that distribution sits. Therefore, standard methods from statistical process control theory can be used to set thresholds for identifying features that should be flagged as potentially defective. Finally, the z-score statistic can be used to "color" maps of features across the array surface, enabling rapid visual identification of groups of aberrant features.

For transformation of raw z-scores into overall metrics that are sensitive to clusters of features that exhibit aberrant signals, it is useful to first process the raw z-score images in a manner that accentuates clustered aberrant feature areas and suppresses isolated aberrant features. One particularly simple method of accomplishing this is to apply a "voting rule" of the following form: If the fraction of z-scores of nearest-neighbors of a particular feature j less than or equal to some threshold $t_z$ is greater than or equal to some threshold $t_f$, flag the feature as occupying a "low z" neighborhood. If the feature itself has a z-score less than or equal to threshold $t_z$, additionally flag the feature as a "low z" feature. Similar rules can be written for "high z" or "outlier z" (i.e. unusually high or low). For a hexagonal grid such as that used for some microarrays, a simple definition of "nearest-neighbors" for an interior feature is the set that includes the feature in question and the hexagon of 6 features immediately surrounding it (the same general definition is used for edge and corner features, except that some of the members of the surrounding hexagon of neighbors are missing). The flag values can also be used to produce array visualizations that are particularly sensitive to the "dark pockets" defect (below).

Once features have been flagged as either "low z" or as being in "low z" neighborhoods, one can calculate a variety of array-wide metrics based on the flags. A particularly useful metric is the percentage of features on the array that are flagged as either exhibiting a low z value or as residing in low z neighborhoods (or both). This metric is strongly correlated to the "median percent CV" family of metrics (see below).

A method of identifying an aberrant feature on a nucleic acid array is therefore provided. In this embodiment, the method may comprise: a) obtaining a log transformed normalized value indicating the amount of hybridization of a test sample to a first feature on the nucleic acid array; b) calculating a z-score for said first feature using: i. the log transformed normalized value; and ii. the distribution of reference log transformed normalized values that indicate the amount of hybridization of control samples to the corresponding feature on a plurality of reference arrays; and c) identifying said test feature as aberrant if it has a z-score that is above or below a defined threshold.

The z-score may be calculated many different ways, e.g., using: a) the median or mean of the distribution, and b) the standard deviation or inter quartile range of the distribution.

In particular embodiments, the z-score indicates how many standard deviations the log transformed normalized value for said first feature is above or below the mean of the reference log transformed normalized values. In this embodiment, the z-score may be calculated using the following formula:

$$z = \frac{x - \mu}{\sigma}$$

where: x is said log transformed normalized value for the first feature; $\mu$ is the mean or median of the reference log transformed normalized values; and $\sigma$ is the standard deviation of the reference log transformed normalized values.

In alternative embodiments, the z-score may be calculated using a scaled interquartile range of the distribution. In these embodiments, the z-score indicates how many scaled interquartile ranges (0.74*IQR) the log transformed normalized value for said first feature is above or below the mean or median of said reference log transformed normalized values.

Depending on the stringency of the test, the defined threshold may be in the range of 4.0 to 8.0, e.g., 5.0 to 7.0, or 5.5 to 6.5, for aberrantly high z-scores, or in the range of −4.0 to −8.0, e.g., −5.0 to −7.0, or −5.5 to −6.5, for aberrantly low z-scores.

The number of control samples that are used to produce the distribution may vary. However, in some embodiments, the reference log transformed normalized values are obtained by hybridizing at least six (e.g., at least 8, at least 10, at least 15, at least 25, at least 100, or up to 100 or more) control samples to reference arrays that contain the feature. The control samples should be from a similar source to that of the test sample, i.e., a source that would be expected to produce a similar gene expression pattern as the test sample. In some embodiments, the control and test sample are obtained from the same tissue (e.g., brain, adrenal gland, skin, lung, spleen, kidney, liver, spleen, lymph node, bone marrow, bladder, stomach, small intestine, large intestine or muscle, etc), bodily fluid (including blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc.) or biopsies of the same type of cancer from different individuals. If the nucleic acid sample is to be made from cell lines, then cell lines containing the same cells (e.g., muscle cells, liver cells, etc.) may be employed. In particular cases, a single sample may be split and used as both a control sample and a test sample and, as such, in certain cases the control sample may be the same as the test sample.

Suitable control datasets may be selected as meeting certain criteria, e.g., consistent feature morphology, signals in an appropriate range (i.e., signals too high (saturated) or too low (not statistically significant)), few population outliers and a low average percent coefficient of variation (% CV) of signals from sets of repeated identical features (see, e.g., van Hijum et al BMC Genomics. 2005 6:77, incorporated by reference, among many others).

In particular cases, the control and test sample are biologically-derived samples. However, in other embodiments, the control and test sample comprises a synthetic oligonucleotide that hybridizes to the feature. In particular embodiments, the nucleic acid array and the reference arrays may be from the same batch or different batches.

The method described may be performed on a plurality of features on an array. In these embodiments, the array may be viewed as a map of colors that indicate the magnitude of the z-scores (i.e., a heat map). In this embodiment, clusters of aberrant features can be identified by eye. In other embodiments, clusters of aberrant features may be identified using nearest neighbor analysis, i.e., by determining whether an aberrant feature has neighbors that are also aberrant.

In these embodiments, the method may comprise: a) obtaining a plurality of log transformed normalized values indicating the amount of hybridization of a test sample to a plurality of features on a nucleic acid array; b) calculating a z-score for each of said features using: i. the log transformed normalized values; and ii. the distribution of reference log transformed normalized values that indicate the amount of hybridization of control samples to the corresponding features on a plurality of reference arrays; and c) identifying any test features of the plurality as being aberrant if they have a z-score that is above or below a defined threshold.

In one embodiment, the control and test sample comprise a mixture of oligonucleotides that hybridize to the features (see, e.g, the oligonucleotides described in U.S. patent application publication US2006012491).

In certain embodiments, the z-scores are calculated using following formula:

$$Z_{i,j} = \frac{S_{i,j} - \mu_S}{\sigma_S}.$$

where: S is the log-transformed, normalized signal, $\mu_S$ is the mean or median of S, $\sigma_S$ is the standard deviation or 0.74*IQR of S, and the indices i and j track array and feature number, respectively.

As noted above, the method may further comprising providing a map of the aberrant features on said array so that said areas of said nucleic acid array that contain clusters of aberrant features can be identified by eye. The method may further comprise performing nearest neighbor analysis on the plurality of features to identify clusters of neighboring aberrant features on said array.

Figure 2:
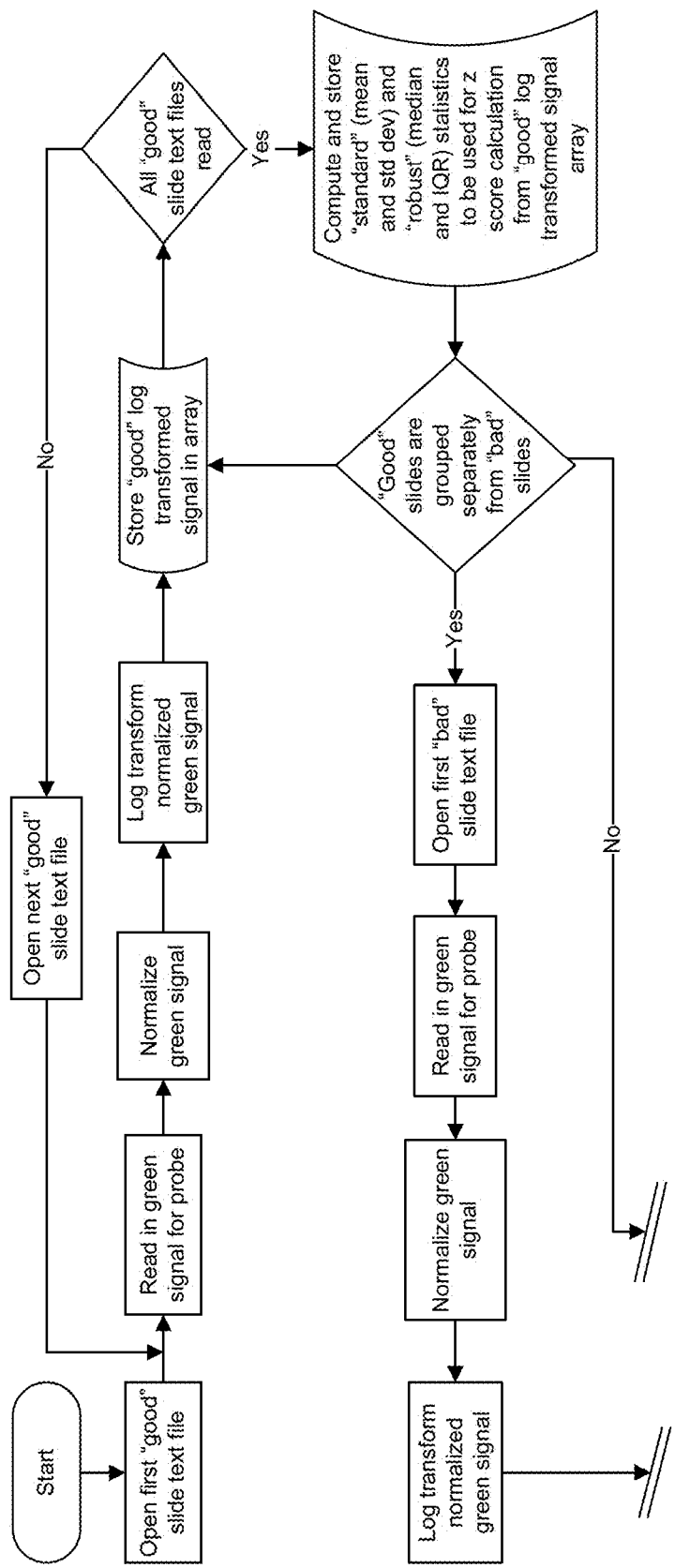
FIG. 2 is a flow chart illustrating some aspects of another embodiment of the subject method.
Figure 2:
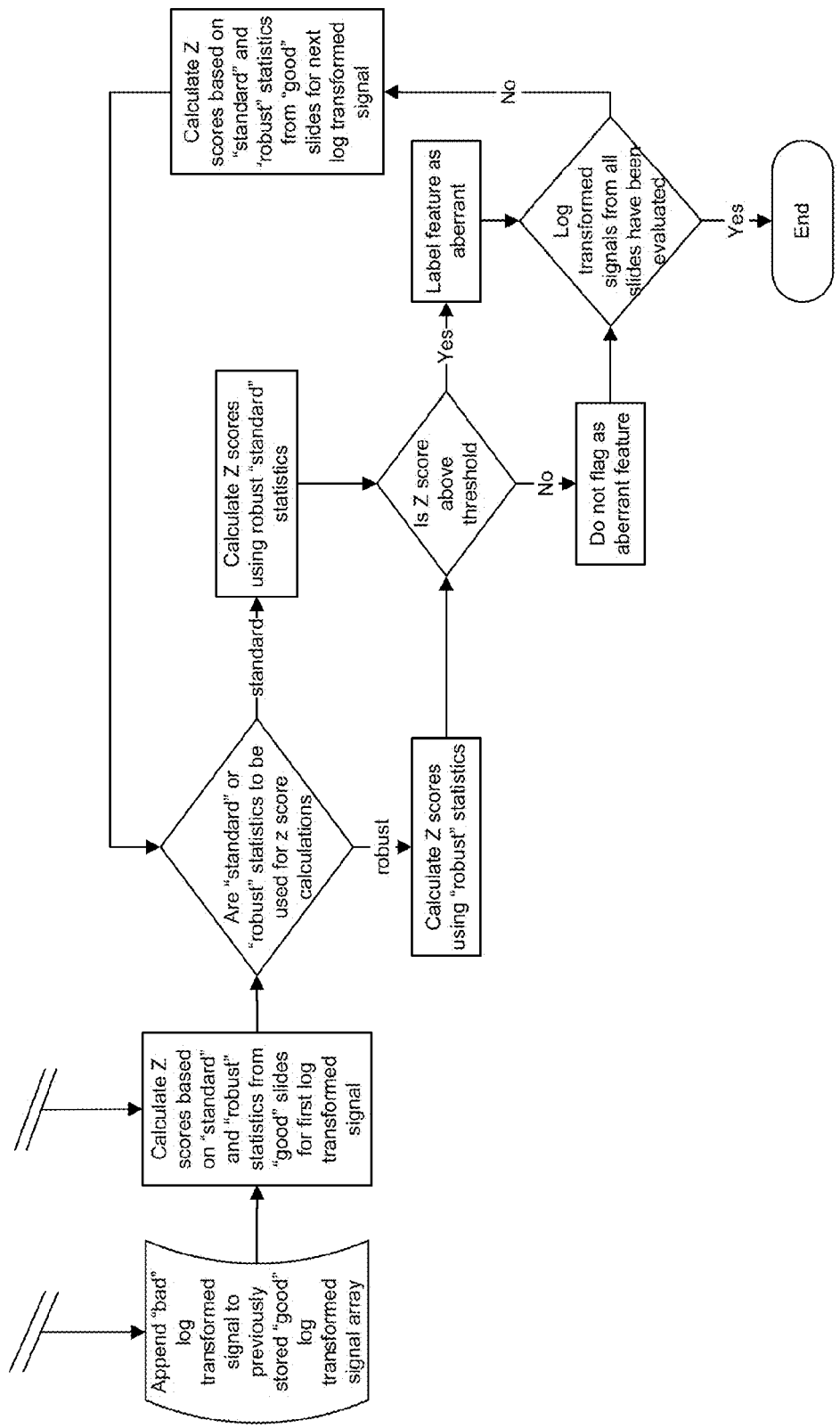

Flow charts that schematically illustrate one embodiment of the instant method are set forth in FIGS. 1 and 2. The data transformations employed in each of the steps in the flow chart are self-explanatory.

In one embodiment, the method may implemented by a computer. A tangible computer-readable medium containing instructions (i.e. "programming") for performing the method described above. The programming can be provided in a physical storage or transmission medium. A computer receiving the instructions can then execute the algorithm and/or process data obtained from the subject method. Examples of storage media that are computer-readable include floppy disks, magnetic tape, DVD, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network. In the context of a computer-implemented method, "obtaining" may be accessing a file that stores data.

EXAMPLE 1

Identification of "Dark Pockets"

"Dark Pockets" are regions of an array where a manufacturing problem may have damaged the probes in the features in that region. These defects can be recognized visually on arrays with narrow signal dynamic ranges (e.g. CGH arrays), but are difficult to recognize on arrays with broader signal dynamic ranges (i.e. most other array application types).

Figure 3:
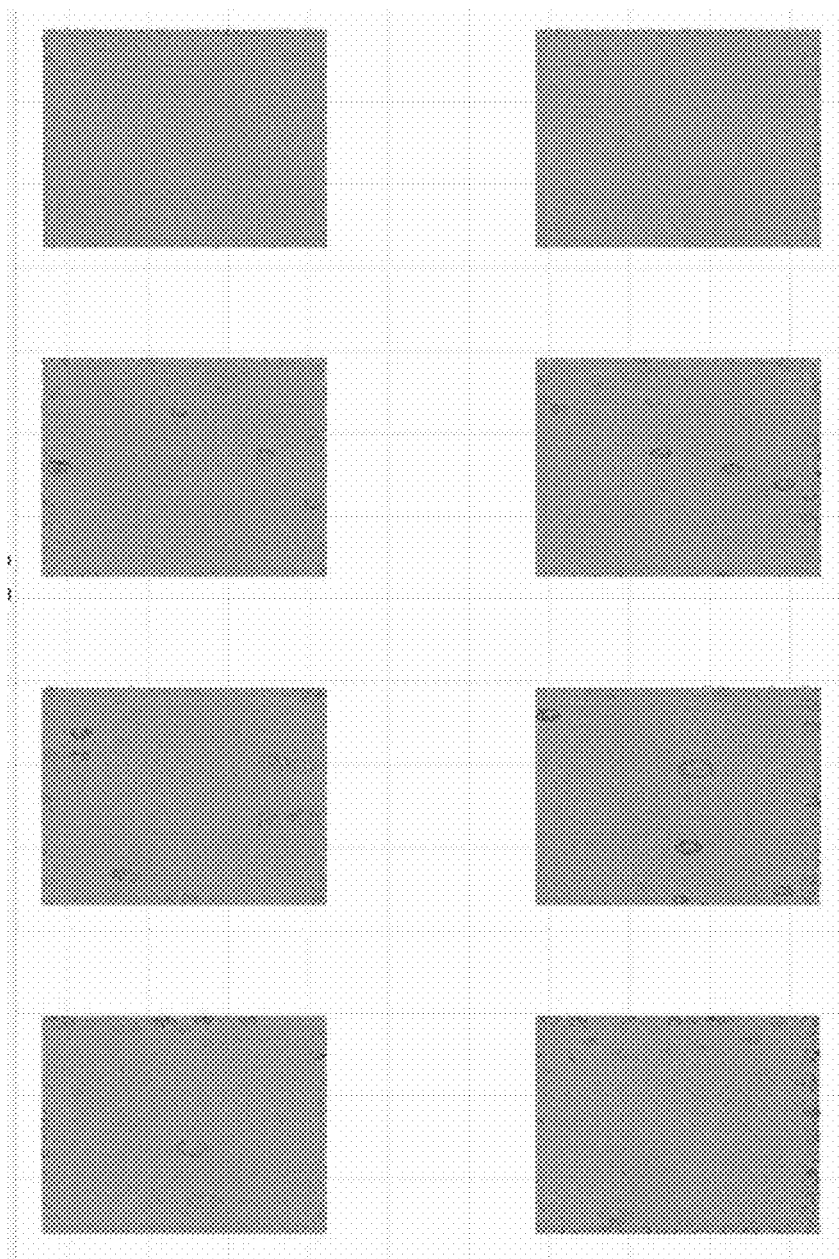
FIG. 3 shows a z-score map of the eight arrays on a high % CV slide.

In the example that follows, data from six "8-pack" "normal" (low % CV) single-color gene expression (GE) arrays and two abnormal (high % CV) arrays were used. No evidence of dark pockets could be seen in the array images themselves. No dark pockets could be observed by z-score visualization of the 8 arrays on one of the normal (low % CV) slides (data not shown). The map for a high % CV slide is shown in FIG. 3.

The visual interpretation of these slides is quite obvious: the normal slides show very few high or low z-scores, and the few aberrant scores observed are not strongly grouped. In stark contrast, there are many regions of clustered, aberrantly low z-scores on the high % CV slide. The number of affected features is easily estimated by counting the number of features with z-scores less than some threshold (e.g., −6). Note that this analysis easily identified the problem of "dark pockets" in spite of the fact that different samples were applied to the different arrays and in spite of the undetectability of the "dark pockets" on scanned array images. These last points demonstrate the method's robustness and sensitivity.

EXAMPLE 2

Conversion of z-Score Maps into Binary "Flag Maps"

Figure 4:
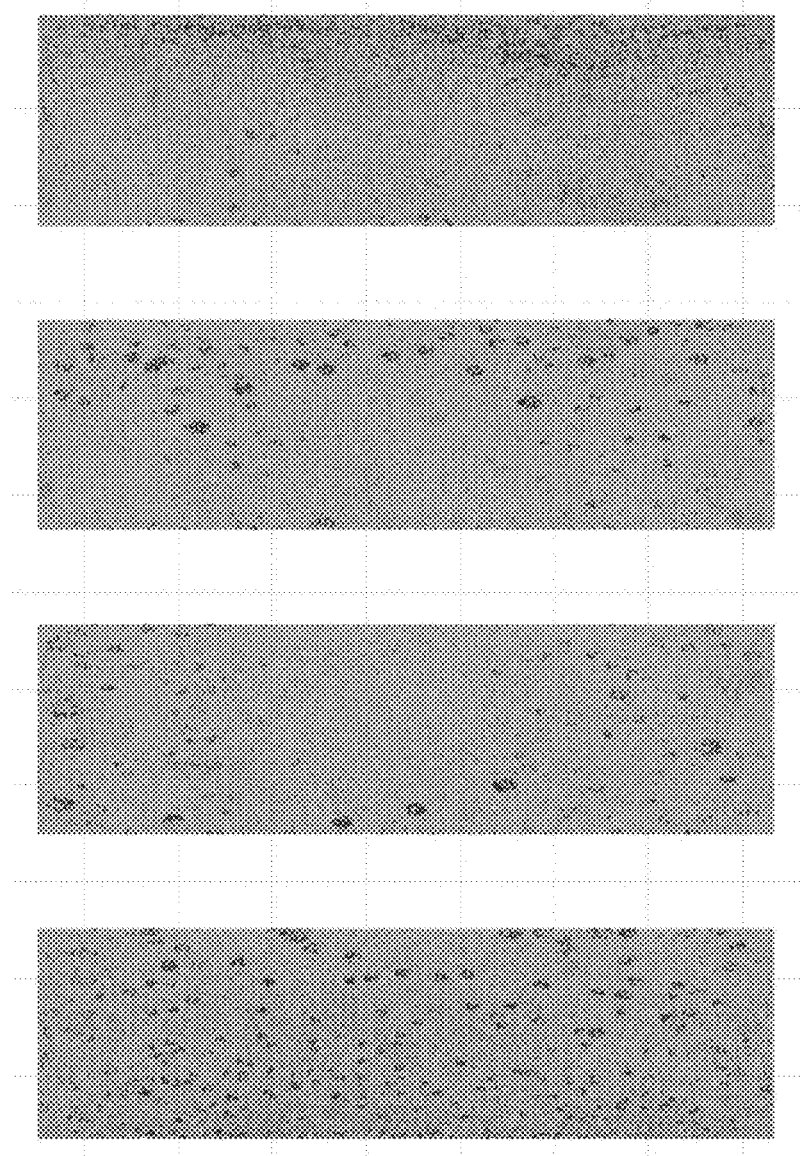
FIG. 4 shows a z-score map of slide 252665211142.

Slide 252665211142 yielded the z-score map (FIG. 4) after hybridization to a sample of labeled, partially degenerate oligos (see US patent application publication no. US20060121491).

Figure 5:
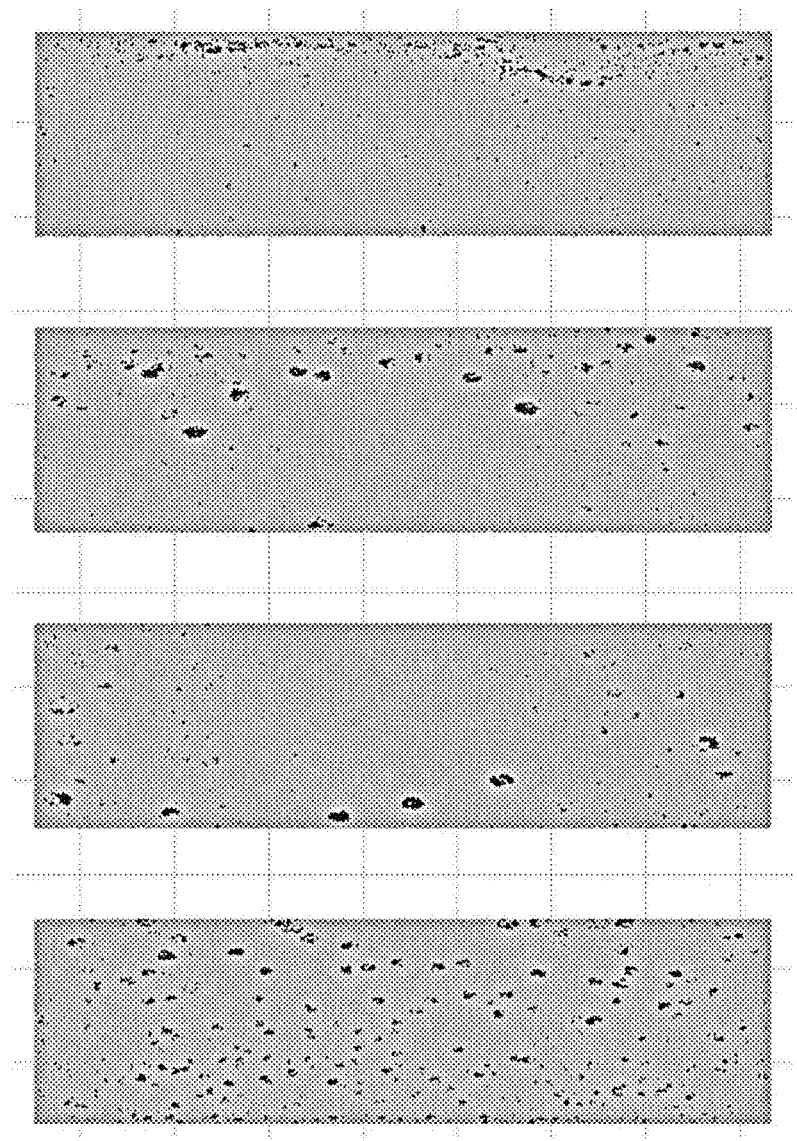
FIG. 5 shows a binary flag map of slide 252665211142.

The data for this map and the flag map that follows were both produced by a computer-implemented method. All arrays were considered as a single group; median and 0.74*IQR used as statistics for normalized log signal distribution center and width, respectively. Features having a z-score≦−5 were flagged as low, and features with a fraction of low nearest neighbors≧0.3 were flagged as occupying "low-z regions". A map of the resulting binary flag vales for "Low-z" and "low-z region" is shown in FIG. 5.

Figure 6:
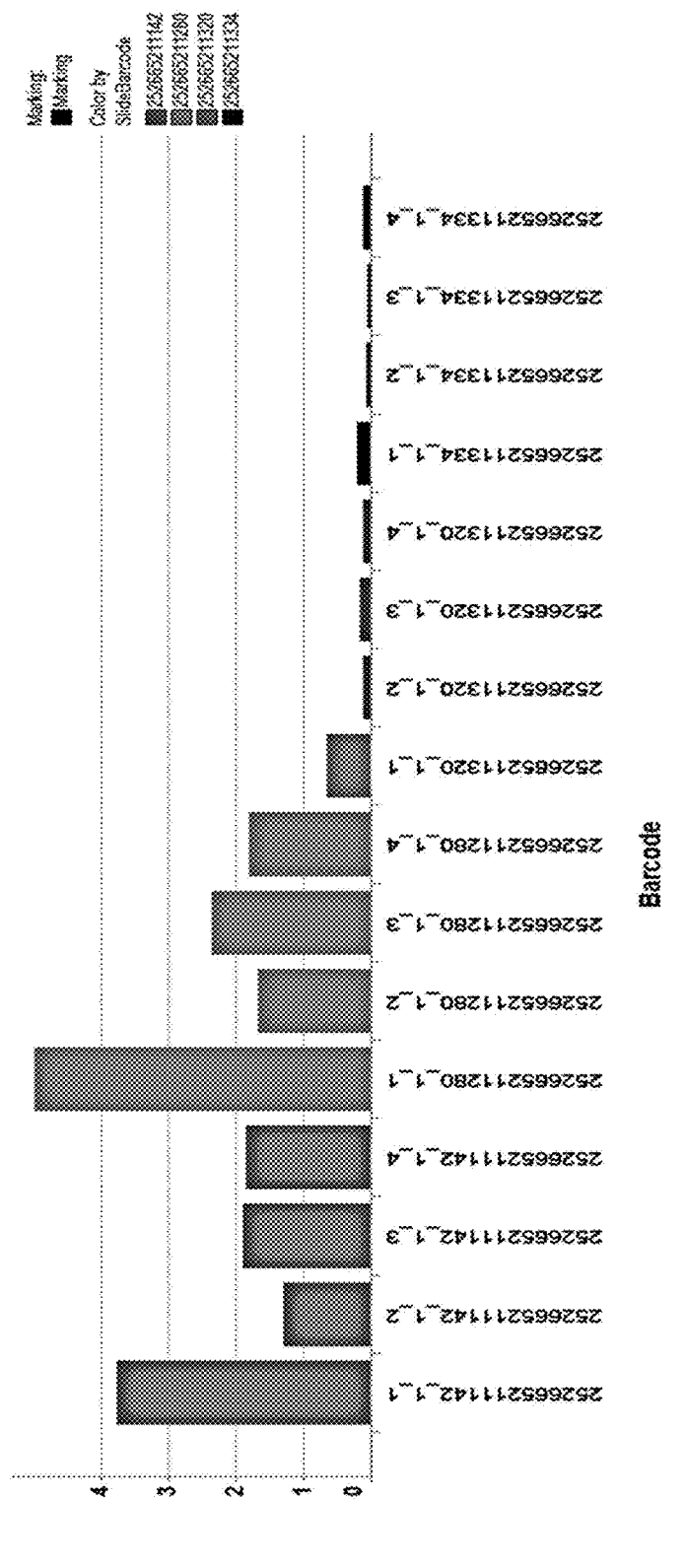
FIG. 6 shows a bar graph of the fraction of features on each array flagged as having a low z-score.

Finally, a bar graph of the fraction of features on each array flagged as having a low z-score, as occupying a low-z neighborhood, or both is shown in FIG. 6, along with values from 3 other slides. The two slides at the left of the graph exhibited "dark pockets"; the two at the right did not.

EXAMPLE 3

Correlation Between Z-Score Metric and Median Percent CV

The fraction of features on each array flagged as having a low z-score, as occupying a low-z neighborhood, or both (z-score metric) is strongly correlated to the median percent CV of the green channel processed signal (data not shown).

This data was obtained by hybridizing arrays made at the same time to a mixture of oligonucleotides sample, feature extracting the data (which generated values for the median percent CV metric), and then analyzing for low-z features and regions. Many of the arrays were also confirmed to exhibit "dark Pockets" by visual inspection.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of identifying an aberrant feature on a nucleic acid array, comprising:
    a) obtaining a log transformed normalized value indicating the amount of hybridization of a test sample to a first feature on said nucleic acid array;
    b) calculating, using a computer, a z-score for said first feature using:
        i. said log transformed normalized value; and
        ii. the distribution of reference log transformed normalized values that indicate the amount of hybridization of control samples to the corresponding feature on a plurality of reference arrays; and
    c) identifying said test feature as aberrant if it has a z-score that is above or below a defined threshold.

2. The method of claim 1, wherein said z-score indicates how many standard deviations the log transformed normalized value for said first feature is above or below the mean or median of said reference log transformed normalized values according to the following formula:

$$z = \frac{x - \mu}{\sigma}$$

wherein:
    x is said log transformed normalized value for said first feature;
    $\mu$ is the mean or median of the reference log transformed normalized values; and
    $\sigma$ is the standard deviation or scaled IQR of the reference log transformed normalized values.

3. The method of claim 1, wherein said z-score indicates how many scaled interquartile ranges (0.74*IQR) the log transformed normalized value for said first feature is above or below the mean or median of said reference log transformed normalized values.

4. The method of claim 1, wherein said reference log transformed normalized values are obtained by hybridizing at least six control samples to reference arrays that contain said feature.

5. The method of claim 1, wherein said control samples are the same as said test sample.

6. The method of claim 1, wherein said control and test sample are biologically-derived samples.

7. The method of claim 1, wherein said control and test sample comprises a synthetic oligonucleotide that hybridizes to said feature.

8. The method of claim 1, wherein said nucleic acid array and said reference arrays are from same batch.

9. The method of claim 1, wherein said nucleic acid array and said reference arrays are from different batches.

10. The method of claim 1, wherein said defined threshold is in the range of 4.0 to 7.0.

11. The method of claim 1, wherein said defined threshold is in the range of 5.0 to 6.0.

12. The method of claim 1, wherein said method comprises:
    a) obtaining a plurality of log transformed normalized values indicating the amount of hybridization of a test sample to a plurality of features on a nucleic acid array;
    b) calculating a z-score for each of said features using:
    i. said log transformed normalized values; and
    ii. the distribution of reference log transformed normalized values that indicate the amount of hybridization of control samples to the corresponding features on a plurality of reference arrays; and
    c) identifying any test features of said plurality as being aberrant if they have a z-score that is above or below a defined threshold.

13. The method of claim 12, wherein said control and test sample comprise a mixture of oligonucleotides that hybridize to said features.

14. The method of claim 12, wherein said z-scores are calculated using following formula:

$$Z_{i,j} = \frac{S_{i,j} - \mu_S}{\sigma_S}.$$

wherein:
    S is the log-transformed, normalized signal,
    $\mu_S$ is the mean or median of S,
    $\sigma_S$ is the standard deviation or 0.74*IQR of S, and
    the indices i and j track array and feature number, respectively.

15. The method of claim 12, further comprising providing a map of said aberrant features on said array so that said areas of said nucleic acid array that contain clusters of aberrant features can be identified by eye.

16. The method of claim 12, further comprising performing nearest neighbor analysis on said plurality of features to identify clusters of neighboring aberrant features on said array.

17. A non-transitory computer readable medium comprising programming for performing the method of claim 1.

* * * * *